US012630857B2

(12) United States Patent
Rovetto et al.

(10) Patent No.: US 12,630,857 B2
(45) Date of Patent: *May 19, 2026

( * ) Notice: Subject to any disclaimer, the term of this patent is extended or adjusted under 35 U.S.C. 154(b) by 24 days.

This patent is subject to a terminal disclaimer.

(54) BIOLOGICAL INDICATOR FOR DETERMINING THE EFFICACY OF A STEAM OR HEAT STERILIZATION PROCESS AND ITS METHOD OF USE

(71) Applicant: Terragene LLC, Spring, TX (US)

(72) Inventors: Adrian Jesus Rovetto, Rosario (AR); Esteban Lombardia, Pueblo Esther (AR); Pablo Ravasi, Rosario (AR)

(73) Assignee: Terragene LLC, Spring, TX (US)

(21) Appl. No.: 18/530,789

(22) Filed: Dec. 6, 2023

(65) Prior Publication Data

US 2024/0110219 A1     Apr. 4, 2024

Related U.S. Application Data

(63) Continuation of application No. 16/543,279, filed on Aug. 16, 2019, now Pat. No. 11,884,960.

(51) Int. Cl.
| | |
|---|---|
| *C12Q 1/22* | (2006.01) |
| *C12N 1/20* | (2006.01) |
| *G01N 21/64* | (2006.01) |

(52) U.S. Cl.
CPC ................. *C12Q 1/22* (2013.01); *C12N 1/20* (2013.01); *G01N 21/6486* (2013.01)

(58) Field of Classification Search
CPC . C12Q 1/22; C12Q 1/04; C12Q 1/045; C12N 1/20; G01N 21/6486; G01N 2333/195; G01N 2333/32; A61L 2/04; A61L 2202/24; A61L 2/07; A61L 2/28
See application file for complete search history.

(56) References Cited

U.S. PATENT DOCUMENTS

| | | | |
|---|---|---|---|
| 5,073,488 | A | 12/1991 | Matner et al. |
| 5,770,393 | A | 6/1998 | Dalmasso et al. |
| 9,717,812 | B2 | 8/2017 | Chandrapati et al. |
| 10,047,334 | B2 | 8/2018 | Chandrapati et al. |
| 11,884,960 | B2 | 1/2024 | Rovetto et al. |
| 2005/0019921 | A1 | 1/2005 | Orwar et al. |
| 2010/0143566 | A1 | 6/2010 | Cagnol et al. |
| 2010/0323386 | A1 | 12/2010 | Lemieux et al. |
| 2012/0021406 | A1 | 1/2012 | Franciskovich et al. |
| 2012/0219600 | A1* | 8/2012 | Perumal ................... B82Y 5/00 |
| | | | 435/40.52 |
| 2014/0220662 | A1 | 8/2014 | Hashman |
| 2014/0370535 | A1 | 12/2014 | Chandrapati et al. |
| 2015/0159192 | A1 | 6/2015 | Foltz et al. |
| 2016/0102335 | A1 | 4/2016 | Franciskovich et al. |
| 2017/0283847 | A1 | 10/2017 | O'Keefe |
| 2017/0292143 | A1 | 10/2017 | Cote et al. |

FOREIGN PATENT DOCUMENTS

| | | |
|---|---|---|
| CA | 2667698 | 7/2008 |
| EP | 2 456 882 | 10/2017 |
| JP | 2014-060947 | 4/2014 |
| WO | WO 2017/185738 | 2/2017 |
| WO | WO 2018/071732 | 4/2018 |

OTHER PUBLICATIONS

Maniara, G et al. Phosphorescence from 2-(p-toluuidinyl)naphthalene-6-sulfonate and 1-anilinonaphthalene-8-sulfonate, commonly used fluorescence probes of biological structures. Photochemistry and Photobiology. 1988. 47(2): 207-208. (Year: 1988).*

Borzova, VA et al. Kinetics of thermal denaturation and aggregation of bovine serum albumin. PLoS One. 2016. 11(4): e0153495. 29 pages. (Year: 2016).*

Terada, H et al. Heat denaturation of serum albumin monitored by 1-anilino-naphthalene-8-sulfonate. Biochimica et Biophysica Acta. 1980. 622(2): 161-170. (Year: 1980).*

Cattoni, Di et al. Kinetics and thermodynamics of the interaction of 1-anilino-naphthalene-8-sulfonate with proteins. Biochimica et Biophysica Acta. 2009. 1794(11): 1700-1708. (Year: 2009).*

Maruthamuthu, M et al. Bromocresol green as a new spectrophotometric probe for serum albumins. Proc. Indian Acad. Sci. (Chem. Sci.). 1988. 100(6): 525-533. (Year: 1988).*

Kragh-Hansen, U et al. Protein binding of small molecules: IV. Relation between binding of phenolsulfophthalein dyes and other ligands with a high affinity for human serum albumin. Biochimica et Biophysica Acta—Protein Structure. 1974. 365(2): 360-371. (Year: 1974).*

(Continued)

*Primary Examiner* — David W Berke-Schlessel
*Assistant Examiner* — Susan E. Fernandez
(74) *Attorney, Agent, or Firm* — Fish & Richardson P.C.

(57)     ABSTRACT

The invention relates to a biological indicator for determining the efficacy of a steam or heat sterilization process, and its method. The biological indicator comprises microbial spores (a), at least one sensor protein exogenous to the microbial spores (b), one fluorophore (c), and a culture medium (d). The invention also refers to the method of use of this biological indicator. This method consists of (a) placing the biological indicator along with a target material to be steam or heat sterilized within a steam or heat sterilizer, (b) carrying out a steam or heat sterilization process, (c) placing the biological indicator in a an incubator, (d) screening the biological indicator for immediate detectable changes in fluorescence intensity, while incubating the biological indicator in the incubator, (e) determining the efficacy of the steam or heat sterilization process based on the screening carried out during step d), (f) extending the incubation of the biological indicator obtained in step d), (g) screening the incubated biological indicators obtained in step e) for an optically detectable color change, and (h) determining the efficacy of the steam or heat sterilization process, according to optically detectable changes obtained in step g).

18 Claims, 2 Drawing Sheets

(56) References Cited

OTHER PUBLICATIONS

Andrea Hawe, Marc Sutter, and Wim Jiskoot: "Extrinsic Fluorescent Dyes as Tools for Protein Characterization"; Pharmaceutical Research, Jul. 2008, vol. 25, Issue 7, pp. 1487-1499.

Collini M, D'alfonso L, Baldini G.: "New insight on beta-lactoglobulin binding sites by 1-anilinonaphthalene-8-sulfonate fluorescence decay"; Protein Science 2000, Oct. 2000, vol. 9, pp. 1968-1974.

D'Alfonso L, Collini M, Baldini G.; "Evidence of heterogeneous 1-anilinonaphthalene-8-sulfonate binding to beta-lactoglobulin from fluorescence spectroscopy"; Biochimica et Biophysica Acta (BBA)—Protein Structure and Molecular Enzymology; Jul. 13, 1999; vol. 1432; Issue 2; pp. 194-202.

Dias et al., "Sterilization of medical devices by ethylene oxide, determination of the dissipation of residues, and use of Green Fluorescent Protein as an indicator of process control," Journal of Biomedical Materials Research Part B: Applied Biomaterials, Nov. 2009, 91B(2):626-630.

Gasymov OK, Glasgow BJ.: "ANS fluorescence: Potential to augment the identification of the external binding sites of proteins"; Biochimica et Biophysica Acta (BBA)—Proteins and Proteomics, vol. 1774, Issue 3, Mar. 2007, pp. 403-411.

Guizelini, BP et al., "Study of the influence of sporulation conditions on heat resistance of Geobacillus stearothermophilus used in the development of biological indicators for steam sterilization, " Arch. Microbial., 2012, 194: 991-999.

International Search Report and Written Opinion in PCT/IB2020/057645, mailed Oct. 22, 2020, 10 pages.

Khalfan et al., "Fluorigenic method for the assay of proteinase activity with the use of 4-methylumbelliferyl-casein," Biochem. J., Jan. 1983, 209:265-267.

Kuznetsova IM1, Sulatskaya A1, Povarova 01, Turoverov KK.: "Reevaluation of ANS Binding to Human and Bbovine Serum Albumins: Key Role of Equilibrium Microdialysis in Ligand—Receptor Binding Characterization"; PLoS One, Jul. 19, 2012, vol. 7, Issue 7, e40845, pp. 1-9.

Mungkarndee et al., "Fluorescence sensor array for identification of commercial milk samples according to their thermal treatments," Food Chemistry, Oct. 2015, 197:198-204.

National Center for Biotechnology Information (2021), "PubChem Compound Summary for CID 1369, 8-Anilino-1-naphthalenesulfonic acid [online]," [retrieved on Sep. 29, 2021], Retrieved from the Internet: <https://pubchem.ncbi.nlm.nih.gov/compound/8-Anilino-1-naphthalenesulfonic-acid>, 30 pages.

Niesen FH, Berglund H, Vedadi M.: "The use of differential scanning fluorimetry to detect ligand interactions that promote protein stability"; Nature Protocols, Sep. 13, 2007, vol. 2, Issue 9, pp. 2212-2221.

Nyman, R et al., "The effect of heat treatment on anilinonaphthalene-8-sulphonate binding to rapeseed albumin (napin)," J. Sci. Food Agric., 1997, 74: 485-489.

Robinson, "Enzymes: principles and biotechnological applications," Essays Biochem, Nov. 2015, 59: 1-41.

Senisterra, G et al., "Thermal denaturation assays in chemical biology," Assay and Drug Development Technologies, 2012, 10(2):128-136.

Togashi, D.M. & Ryder, A.G.: "A Fluorescence Analysis of ANS Bound to Bovine Serum Albumin: Binding Properties Revisited by Using Energy Transfer"; Journal of Fluorescence, Mar. 2008, vol. 18, Issue 2, pp. 519-526.

Uversky VN1, Winter S, Lober G.: "Use of fluorescence decay times of 8-ANS-protein complexes to study the conformational transitions in proteins which unfold through the molten globule state"; Biophysical Chemistry, Jun. 11, 1996; vol. 60, Issue 3, pp. 79-88.

Watanabe et al., "Biosensing Probe for Quality Control Monitoring of the Structural Integrity of Therapeutic Antibodies," Analytical Chemistry, Oct. 2016, 88(20):10095-10101.

* cited by examiner

1

BIOLOGICAL INDICATOR FOR DETERMINING THE EFFICACY OF A STEAM OR HEAT STERILIZATION PROCESS AND ITS METHOD OF USE

CROSS-REFERENCE TO RELATED APPLICATIONS

This application claims priority to pending U.S. application Ser. No. 16/543,279, filed Aug. 16, 2019, the contents of which are incorporated herein by reference in their entirety.

FIELD OF THE INVENTION

The present invention refers to biological indicators suitable for determining the outcome of a steam or heat sterilization process.

BACKGROUND OF THE INVENTION

Sterilization processes are aimed at providing surfaces or objects (e.g. laboratory or medical devices, instruments or utensils) that are free of viable forms of life. Such processes are used extensively in contexts like the healthcare industry or a wide range of scientific research activities.

A central aspect of such processes is the ability to determine whether the sterilization process was successful, in order to ensure the required conditions of use of the sterilized material and/or surface. To this end, several methods are employed with varying degrees of quality.

Biological indicators known in the art generally involve subjecting a known amount of microbial spores, such as bacterial spores, to a sterilization process along with the target material and/or surface. Immediately after the process is complete, tests are carried out in order to probe the presence of remaining living and/or viable microorganisms. If these tests yield negative results, then it may be determined that the sterilization was effective.

More specific biological indicators include probing the occurrence of certain biochemical reactions that are known to indicate the presence of viable forms of life. Such biochemical reactions relate to enzymatic and/or catalytic activity commonly found in microbial life or color change in a dye.

Patent application US 2015/0159192 A1 discloses a method of determining the success of a sterilization process comprising the use of an isolated enzyme or the microorganism to which such enzyme is endogenous or expressed by genetic engineering. Indicator enzymes according to this disclosure are enzymes found commonly in spore forming microorganisms such as beta-D-glucosidase. After the indicator has been exposed to a sterilizing process, an enzymatic activity test is carried out in order to assess the effectiveness of the sterilization.

Other biological indicators are based on the use of genetically engineered microorganisms capable of expressing specific reporter genes.

Patent application WO 2018/071732 A1 discloses a biological indicator making use of genetically engineered microorganisms capable of expressing reporter genes that are suitable to be screened for fluorescence (e.g. reporter genes suitable for expression of fluorescent proteins). After the indicator has been subjected to the sterilization process, it is screened for optically detectable signals, thus evidencing the presence or absence of viable microorganisms.

Similarly, patent application WO 2017/185738 A1 discloses a biological indicator based on the use of spores from genetically engineered microorganisms expressing specific fluorescent reporter genes. After the sterilization process, the indicator is screened for optically detectable signals, in order to assess the presence of viable microorganisms.

Other biological indicators known in the art comprise providing a genetically engineered microorganism suitable for expression of specific enzymes, in order to screen enzymatic activity of said specific enzyme after sterilization.

Patent application US 2017/0292143 A1 discloses genetically engineered microorganisms suitable for expression of a specific enzyme (e.g. β-lactamase) which is able to hydrolyze a fluorogenic compound designed to emit fluorescence by hydrolysis. The optically detectable fluorescent signal therefore indicates the presence of viable microorganisms.

Other biological indicators employ the screening of surrogate proteins selected from proteins critical for the growth of infectious agents, and pathogenic or immunogenic proteins.

Patent application US 2017/0283847 A1 discloses a biological indicator based on the screening for a defined surrogate protein after a sterilization process. The disclosed method requires procedures such as Western Blot analysis in order to assess the presence of the target protein.

Other biological indicators of similar characteristics also employ genetically modified microorganisms or mutant and/or labeled proteins and/or enzymes in order to enable an effective screening after sterilization, such as disclosed by CA 2667698 C, U.S. Pat. No. 9,717,812 B2, EP 2456882 B1, U.S. Ser. No. 10/047,334 B2, US 20140370535 A1 and JP 2014-060947 A.

The biological indicators of the previous art generally rely on complex, costly and significantly time-consuming procedures for both production and use, affecting the overall costs of the biological indicator per se and of sterilization processes in general. Biological indicators based on such procedures demand considerable incubation and/or readout time, which also represents a significant expense in time and resources. Biological indicators that rely solely on screening enzymatic activity are limited by the generally low stability of the employed enzyme. Inherent characteristics of enzymes, like their structure and catalytic activity, have a negative effect on the overall stability of the indicator system, increasing the amount of false positives. Moreover, longer periods of time are needed in order to screen enzymatic activity.

Therefore, the need remains for a biological indicator that is both reliable and cost-effective, capable of reducing incubation and/or readout times, and without involving costly procedures and/or requirements.

The present invention does not rely on genetically engineered microorganisms or modified recombinant proteins, which are costly to obtain and mass-produce.

Additionally, the present invention does not require development stages comprising Western Blot analysis, protein array analysis, magnetic separation analysis, mass spectrometry analysis, peptide analysis, chromatography analysis, nor gas chromatography analysis, which require specialized equipment and are considerably time-consuming.

On the other hand, the fact that the biological indicator does not depend on enzymatic reactions to indirectly determine the outcome of a sterilization process provides more reliable results. Enzymatic reactions are complex physical and chemical phenomenons that require a wide range of favorable conditions in order to take place. For example, and as is known to a person skilled in the art, enzymatic activity depends greatly on the structure and nature of an enzyme's active site. Even a small variation in any of the characteristics of such active sites, o in the environmental conditions around the enzyme, may have significant consequences in the enzyme's ability to properly carry out the reaction. The chances of such variations entails serious potential flaws for a biological indicator reliant on enzymatic reactions, as these might incorrectly indicate the success of a sterilization.

BRIEF DESCRIPTION OF THE INVENTION

The present invention relies only on the results of two simple and straightforward tests, namely a fluorescence intensity test and a colorimetric test, rendering the whole process significantly more time- and cost-effective in relation to the prior art.

In a first aspect, the present invention relates to a self-contained biological indicator for determining the efficacy of a steam or heat sterilization process, employing both an immediate fluorescence signal detection and colorimetric test after a certain incubation time.

It is therefore an object of the present application a device for determining the efficacy of a steam or heat sterilization process comprising a flexible container, comprising:
    a) a set of microbial spores,
    b) at least one sensor protein exogenous to the microbial
       spores,
    c) a fluorophore, and
    d) a culture medium.
    e) a PH indicator or colorimetric component for extended
       readout confirmation.

In an embodiment of the invention, the set of microbial spores in a) are bacterial spores.

In a preferred embodiment of the invention the set of microbial spores in a) are bacterial spores selected from the group comprising *B. atrophaeus, B. subtilis, G. stearothermophilus*, and *B. pumilus*.

In a preferred embodiment of the present invention, the microbial spores are embedded in a carrier.

In another preferred embodiment of the present invention, the sensor proteins exogenous to the microbial spores are also embedded in the carrier.

In another preferred embodiment of the present invention, the sensor proteins exogenous to the microbial spores are contained in a breakable ampoule.

In another embodiment of the invention, the sensor proteins exogenous to the microbial spores are selected from the group comprising: fibrin, elastin, casein, collagen, actin, keratin, albumin. Enzymes like lysozyme, amylase, lipase, pepsin, glucosidase, phosphatase, galactosidase, chymotrypsin and lipase can also be used, but only due to their structural features, not in relation to their catalytic activity.

In a preferred embodiment of the present invention, the fluorophore is contained in a breakable ampoule.

In an embodiment of the invention, the fluorophore c) is selected from the group comprising: Nile red; coumarin 6H; coumarin 6; coumarin 30; coumarin 102; coumarin 153, 7-Amino-4-(trifluoromethyl) coumarin; 8-anilinonaphthalene-1-sulfonic acid; 7-hydroxy-4-(trifluoromethyl) coumarin; 4,4'-dianilino-1,1'-binaphthyl-5,5-disulfonic acid dipotassium salt; L-alanine-7-amido-4-methylcoumarin; L-proline-7-amido-4-methylcoumarin; L-tyrosine-7-amido-4-methylcoumarin; L-leucine-7-amido-4-methylcoumarin; and L-phenylalanine-7-amido-4-methylcoumarin.

In a preferred embodiment of the present invention, the culture medium is contained in a breakable ampoule.

In another embodiment of the invention, the culture medium components comprise bacteriological peptone, yeast extract and L-valine.

In a preferred embodiment of the present invention, the culture medium comprises a colorimetric component.

In an embodiment of the present invention, the colorimetric component of the culture medium is selected from a group comprising bromocresol purple, bromocresol green, phenol red, thymol blue, bromophenol blue, bromothymol blue, 6-chloro-3-indoxyl-alpha-D-glucopyranoside, 5-bromo-4-chloro-3-indolyl α-D-glucopyranoside, 6-chloro-3-indoxyl-beta-D-galactopyranoside, 5-bromo-4-chloro-3-indolyl β-D-galactopyranoside, 5-bromo-4-chloro-3-indoxyl phosphate.

In a yet more preferred embodiment of the present invention, the sensor proteins exogenous to the microbial spores, the fluorophore, and the culture medium are contained in a single breakable ampoule, in order to minimize chances of contamination due to excessive manipulation or handling of the biological indicator.

In a preferred embodiment of the present invention, the breakable ampoule is made of a material with low thermal expansion coefficient, preferably borosilicate glass.

In a second aspect of the invention, another object is a method of use of the previously described biological indicator of the invention, said method of use generally comprising:
    a) placing the biological indicator along with a target
       material to be steam or heat sterilized within a steam or
       heat sterilizer,
    b) carrying out a steam or heat sterilization process,
    c) placing the biological indicator in an incubator,
    d) screening the biological indicator for immediate detectable changes in fluorescence intensity, while incubating
       the biological indicator in the incubator,
    e) determining the efficacy of the steam or heat sterilization process based on the screening carried out during
       step d),
    f) extending the incubation of the biological indicator
       obtained in step d),
    g) screening the incubated biological indicators obtained
       in step e) for an optically detectable color change, and
    h) determining the efficacy of the steam or heat sterilization process, according to optically detectable changes
       obtained in step g).

In an embodiment of the method of the present the invention, in steps a) and b) the biological indicator is placed within a steam or heat permeable package inside the steam or heat sterilizer alongside the target material.

In a preferred embodiment of the method of the present invention, the previously prepared incubator is a market available incubator, selected from the group comprising Terragene Incubator Reader Bionova® (IC10/20FR or IC10/20FRLCD) or MiniBio.

In another embodiment of the method of the present invention, in step c) the previously prepared available incubator is set at a temperature in the range of 55-65° C., preferably 58-62° C., yet more preferably 60° C.

In an embodiment of the method of the present invention, in step c) the ampoule is crushed immediately before the biological indicator is placed within the previously prepared incubator.

In an embodiment of the method of the present invention, during step d) the biological indicator is screened for changes in fluorescence intensity, immediately after sterilization and while starting incubation.

In an embodiment of the method of the present invention, during step g) the efficacy of the steam or heat sterilization process is determined according to the results obtained from both steps d) and g). A positive result in any one of steps d) or f) indicates an incomplete or failed sterilization process.

DETAILED DESCRIPTION OF THE INVENTION

The device comprises a set of microbial spores, at least one sensor protein exogenous to the microbial spores, at least a fluorophore, and a culture medium.

The biological indicator is a self-contained device, which means that the set of microbial spores, the one or more sensor proteins exogenous to the microbial spores, the fluorophore and the culture medium are contained within a single flexible container, which helps avoiding possible contaminations due to manipulation. The culture medium is nonetheless separated from the set of microbial spores, within a breakable ampoule contained in the flexible container, due to the need to bring these two elements into contact only after the sterilization process is complete.

Figure 2:
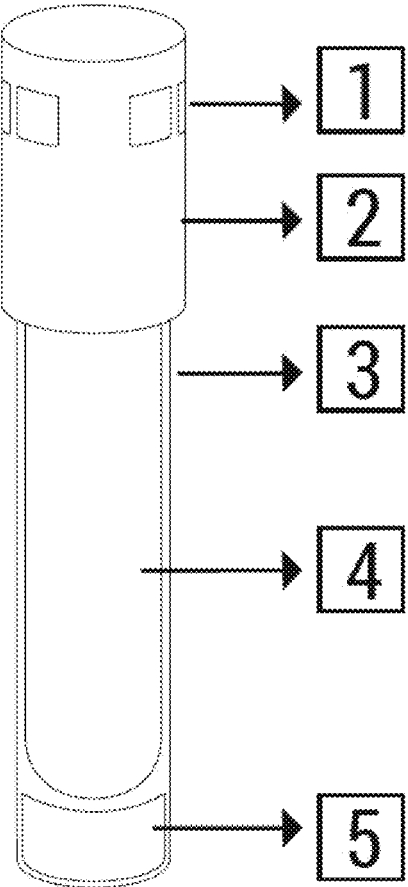
FIG. 2 shows a schematic side view of the biological indicator of the invention.

In an embodiment of the invention, the biological indicator comprises a flexible container as schematized in FIG. 2, comprising a cap 2 for sealing the flexible container, cap orifices 1, a container tube 3, an ampoule 4 containing culture medium and a carrier 5 containing the microbial spores.

In certain embodiments, the flexible container is a translucent polypropylene tube.

In another embodiment, the flexible container comprises a mobile cap that may be pushed down in order to seal the container.

In other embodiments, the microbial spores are embedded in a carrier contained within the flexible container.

In certain embodiments, the microbial spores are embedded in a carrier made of a porous material, such as cellulose, polypropylene fibers material, high-density polyethylene fibers, or in the polypropylene container itself.

In a preferred embodiment, the cellulose carrier is a sheet of paper with a grammage of 130 to 180 $g/m^2$.

In an embodiment of the present invention, the ampoules are made of a fragile material with low thermal expansion coefficient, such as borosilicate glass, preferably glass, and contain 0.5 to 0.9 ml of culture medium.

In a preferred embodiment, the culture medium comprises 0.8 to 1.2 g/L of bacteriological peptone; 0.8 to 1.2 g/L of yeast extract and 0.4 to 0.6 g/L of L-valine.

In a preferred embodiment, the culture medium comprises 0.03 g/L of bromothymol blue indicator as a colorimetric component. Said culture medium has an adjusted pH around 7.5. In a particular preferred embodiment, the pH is adjusted with sodium hydroxide.

In some embodiments, detection of a change in fluorescence intensity as a result of an interaction between the fluorophore and the at least one sensor protein exogenous to the microbial spores may be achieved by means of a fluorimeter.

In a preferred embodiment of the invention, the fluorimeter is integrated in the same incubator, in order to minimize handling and movement of the biological indicator. This way, the detection of a change in fluorescence intensity can be made directly in the same incubator, without requiring further steps to obtain a fluorescence readout.

In some embodiments, detection of a change in color as a result of a colorimetric test may be achieved by means of direct visual observation or by means of a camera with subsequent image analysis.

The at least one sensor protein exogenous to the microbial spores and the fluorophore may be contained in either the cellulose carrier or the ampoule.

In a preferred embodiment of the invention, the at least one sensor protein exogenous to the microbial spores and the fluorophore are contained in the ampoule.

While contained in the sealed ampoule, the at least one sensor protein exogenous to the microbial spores and the fluorophore are subject to the same temperature conditions as the target material to be sterilized. This is due to the fact that the effect of the sterilization process on the exogenous sensor protein structure is achieved by means of heat. Direct contact with steam or heat is not required for the exogenous sensor proteins to reach the desired temperature in order to undergo structural changes.

The at least one sensor protein exogenous to the microbial spores is present in a concentration range of 0.05-0.8 g/ml, preferably 0.5 g/ml. Said at least one sensor protein exogenous to the microbial spores is selected from the group comprising fibrin, elastin, casein, collagen, actin, keratin, albumin. Enzymes like lysozyme, amylase, lipase, pepsin, glucosidase, phosphatase, galactosidase, chymotrypsin and lipase can also be used, but only due to their structural features, not in relation to their catalytic activity. This at least one sensor protein exogenous to the microbial spores can interact differentially with the fluorophores depending on their tridimensional structure. Said tridimensional structure is closely related to conditions of the steam or heat sterilization process, such as exposition and moisture. Time of exposure to said conditions is also an important factor influencing said tridimensional structure.

Figure 1:
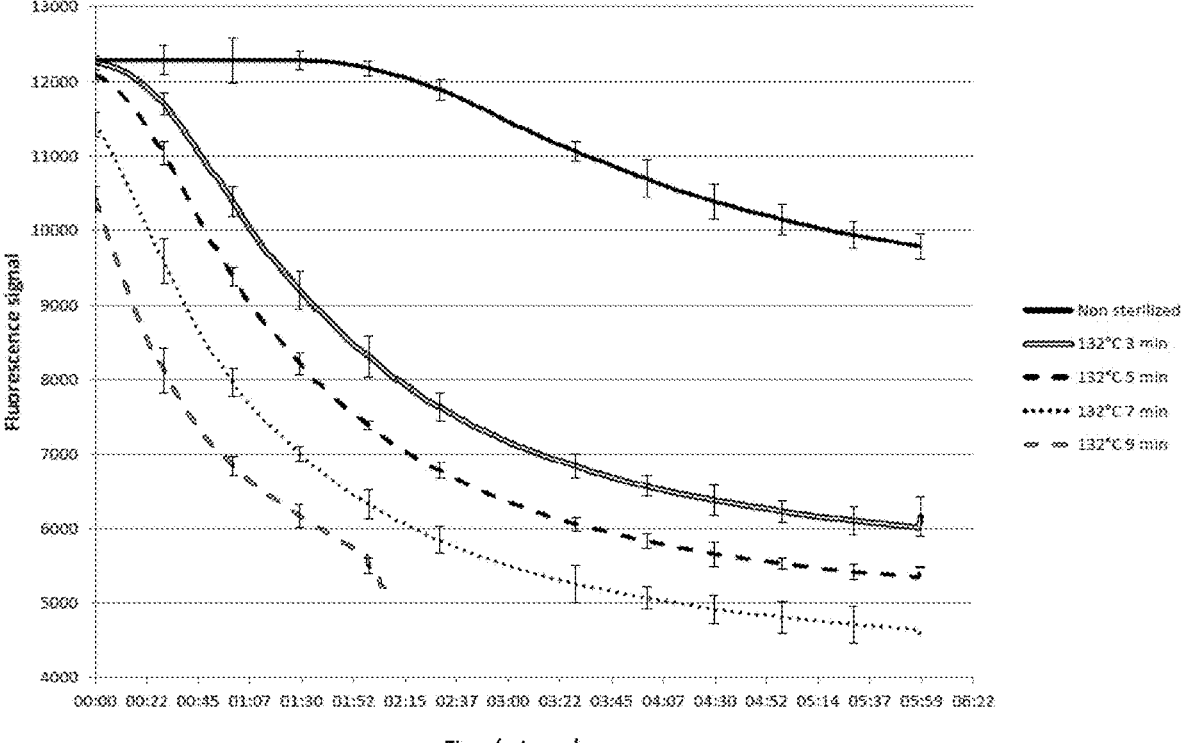
FIG. 1 shows the fluorescence intensity as a function of time since the start of the incubation step. Each curve corresponds to different sterilizing times: 3, 5, 7 and 9 minutes, at the same fixed sterilization temperature of 132° C. The non-sterilized condition is also shown. As the sterilization time increases, the slope of the corresponding curve is significantly more prominent. A longer exposition to high temperatures allows for more energy to be transferred to the biological indicator, which in turn results in a more significant fluorescence intensity change. Specifically, a longer exposition time results in a more drastic fluorescence intensity decrease.

As seen in FIG. 1, at the temperature at which the steam or heat sterilization processes are usually carried out, i.e. 132° C., a change in fluorescence is observed later due to changes in protein tridimensional structure. These changes take place faster when they are preceded by longer times of sterilization. Longer sterilization times cause a more thorough and widespread denaturation of the exogenous sensor proteins, impairing their ability to bind to the fluorophore. The fluorophore is therefore released and left to interact with the polar aqueous medium. This interaction yields a substantially less fluorescent signal that its previous interaction with the structurally intact proteins.

It is noteworthy that the change in a protein's tridimensional structure due to exposition to high temperatures may have varying effects on its ability to bind the fluorophore. Affinity may increase or decrease, resulting in an increasing or decreasing fluorescent signal. The resulting fluorescence change depends on the specific protein and fluorophore selected to carry out the test.

A person skilled in the art will recognize that changes in the tridimensional structure of proteins exposed to high temperatures are necessarily linked to the death of microorganisms that undergo the same exposure (since life is unsustainable for a microorganism when all or a significant majority of its constituent proteins are denatured). As such, a change in the tridimensional structure of the exogenous sensor proteins of the present invention indicate the death of any living microorganism, including microbial spores.

In the biological indicator of the present invention, the denaturation of the sensor protein exogenous to the microbial spores is therefore directly correlated with the death of the microbial spores. Consequently, the change in fluorescence resulting from the sensor protein denaturation guarantees the prediction of death of the spore population contained in the biological indicator.

In an embodiment of the invention, the fluorophore is present in a concentration in a range of 0.07-0.2 mg/ml, preferably 0.1 mg/ml. Said fluorophore is selected from the group comprising: Nile red; coumarin 6H; coumarin 6; coumarin 30; coumarin 102; coumarin 153, 7-Amino-4-(trifluoromethyl) coumarin; 8-anilinonaphthalene-1-sulfonic acid; 7-hydroxy-4-(trifluoromethyl) coumarin; 4,4'-dianilino-1,1'-binaphthyl-5,5-disulfonic acid dipotassium salt; L-alanine-7-amido-4-methylcoumarin; L-proline-7-amido-4-methylcoumarin; L-tyrosine-7-amido-4-methylcoumarin; L-leucine-7-amido-4-methylcoumarin; and L-phenylalanine-7-amido-4-methylcoumarin.

In one embodiment, the protein/fluorophore ratio contained in the biological indicator is between 2:1 and 8:1.

In a preferred embodiment, the protein/fluorophore ratio contained in the biological indicator is 5:1.

These fluorophores are able to interact with different regions of the sensor proteins exogenous to the microbial spores, depending on their tridimensional structure and the polarity of the protein's environment. In relation to the temperature, moisture and time of exposure of the steam or heat sterilization process, the sensor proteins exogenous to the microbial spores display different tridimensional structures, which in turn involve different interactions with the fluorophores, resulting in variable fluorescence emission intensity. This is an instantaneous phenomenon that can be detected immediately, or in a very short incubation time.

The reliance of the biological indicator on this particular phenomenon allows for immediate or instantaneous results. Therefore, if desired, determination of the efficacy of a steam or heat sterilization process is available instantly without having to invest in lengthy incubation times or costly procedures. In this case, time for enzyme catalytic activity is not necessary. The detectable change rate of a protein's tridimensional structure subjected to high temperatures can be measured instantly, as opposed to measuring an enzymatic reaction.

The top of the container comprises a medical grade paper, permeable to the sterilizer agent and a polypropylene cap with lateral openings. The device has been described in detail with reference to the accompanying FIG. 2.

Preferably, all elements are sterilized prior to assembly with ethylene oxide 800 mg/ml for 2 hours. Said elements are then assembled in sterile conditions, with the spore containing carrier being inoculated with the spores prior to assembly in sterile conditions as well.

The method of use of the biological indicator will be described as follows and will be illustrated by means of non-limiting examples.

The method of the present invention comprises
a first step wherein the biological indicator is placed along with the target material to be steam or heat sterilized within a steam or heat sterilizer,
a second step wherein the steam or heat sterilization process is carried out at 90° C.-145° C.,
a third step wherein the biological indicator is placed in a previously prepared incubator set at a temperature in the range of 55-65° C., preferably 58-62° C., yet more preferably 60° C., and the ampoule is broken by crushing it immediately after the biological indicator is placed within the incubator,
a fourth step wherein the biological indicator is screened for optically detectable changes in fluorescence intensity, immediately after being placed in the previously prepared incubator, while incubation of the biological indicator in the previously prepared incubator is ongoing,
a fifth step wherein the efficacy of the steam or heat sterilization process is determined according to the fluorescence intensity screening results of the fourth step,
a sixth step wherein the biological indicator is incubated for 24 hours-168 hours at a temperature in the range of 55-65° C., preferably 58-62° C., yet more preferably 60° C.,
a seventh step wherein the culture medium obtained in the sixth step is readout with a colorimetric component, screening for optically detectable changes in color 24-168 hours;
a last step wherein the efficacy of the steam or heat sterilization process is determined according to the results of the colorimetric screening of the seventh step.

In a particular embodiment of the method of the present invention, the biological indicator is placed in a package along with the material to be sterilized. The package is located inside a steam or heat sterilizer besides the target material to be sterilized in order to ensure that the biological indicator undergoes the same sterilization conditions as the target, related to the position and temperature within the steam or heat sterilizer.

In another particular embodiment, the biological indicator is placed in the areas that are previously considered more inaccessible to the sterilizer agent. Then, the sterilization is done in the usual way. During this step, the cap of the biological indicator container is loose (i.e. the tube is not entirely sealed by the cap). In certain embodiments, the sterilization is done at 90° C.-145° C. After the steam or heat sterilization process is finished, the biological indicator is removed from the package and left to cool until it reaches room temperature. An incubator is previously prepared for the readout and detection steps.

In a preferred embodiment, the incubator is capable of measuring fluorescence intensity by means of an integrated sensor. In a yet more preferred embodiment of the invention, the incubator is selected from the group consisting of Terragene Incubator Reader Bionova® IC10/20FR, IC10/20FRLCD or MiniBio. The incubator is set at a temperature in the range of 55-65° C., preferably 58-62° C., yet more preferably 60° C. Once the desired temperature is reached, the cap is pressed to seal the tube, the ampoule is crushed, and the biological indicator is placed inside the previously prepared incubator. When the ampoule is crushed, the different components of the biological indicator are brought into contact. The ampoule should not be broken before the incubator reaches the desired temperature.

Immediately after being placed inside the incubator, the processed biological indicator yields an instantaneously detectable fluorescence signal. In a particular embodiment of the invention, the used wavelength is $\lambda_{exc}$=340-380 nm/$\lambda_{em}$=455-465 nm.

In a particular embodiment of the invention, an effective sterilization is evidenced if fluorescence values change drastically (accordingly with the irreversible modification of the protein structure). If after 0 to 120 seconds of incubation an important change of fluorescence intensity is detected, it means that the sterilization was effective, sufficiently affecting the tridimensional structure of sensor proteins exogenous to the microbial spores and changing the fluorophore environment.

The incubation at a temperature in the range of 55-65° C., 58-62° C., or 60° C. continues to allow the microbial spores growth in order to perform the colorimetric test for 24-168 hours. In a particular embodiment of the invention, if the sterilization was ineffective, the microbial spores are viable and therefore grow, whereby the culture medium changes color. This phenomenon is due to the varying medium pH or the metabolic enzyme activity with colorimetric components caused by the growth of microbial life, as is well known in the art.

The sterilization efficacy will be determined both by the optically observed change in fluorescence and by the optically observed change in the culture medium. In a particular embodiment, a positive control should be used to observe and compare the change in color and the presence of fluorescence.

EXAMPLES

Example 1

The example was carried out using an F. & M. Lautenschläger GmbH & Co. resistometer, which allows to conduct sublethal time expositions in order to evaluate predictions of a biological indicator.

BIONOVA BT224 biological indicators, which are the fastest indicators currently available in the market, were used for testing during the example along with the biological indicator of the present invention in order to obtain comparison data.

Fast readouts were obtained using an IC10/20FRLCD incubator. Extended readouts (7 days) were carried out in humidity chambers with 80% relative humidity at 60° C.

Culture medium contained in the ampoules of the biological indicator of the invention consisted of 1 g/L of bacteriological peptone; 1 g/L of yeast extract and 0.5 g/L of L-valine.

Fluorescence readouts with the biological indicator of the invention were carried out within 0-20 seconds according to the method of the invention.

20 biological indicator of the invention and 20 control indicator tests were carried out for each particular exposure time.

Ampoule contents of the biological indicator of the invention were as follows: Bromothymol blue was used as colorimetric component of the culture medium and 0.1 mg/ml L-tyrosine-7-amido-4-methylcoumarin as fluorophore. 0.5 g/ml casein was employed as exogenous sensor protein.

Along with the ampoule, the carrier containing $2.5 \times 10^6$ CFU of *Geobacillus stearothermophilus* ATCC 7953 spores was laid inside the tube. Exposure times were conducted at 132° C. according to the method of the invention.

| Exposure Time (seconds) | Positives Instant readout | Positives 7 days readout | Positives 20 min readout BIONOVA BT224 | Positives 7 days readout BIONOVA BT224 |
|---|---|---|---|---|
| 120 | 20/20 | 20/20 | 20/20 | 20/20 |
| 150 | 20/20 | 16/20 | 20/20 | 14/20 |
| 180 | 13/20 | 4/20 | 15/20 | 5/20 |
| 210 | 3/20 | 0/20 | 5/20 | 0/20 |
| 240 | 0/20 | 0/20 | 0/20 | 0/20 |

Example 2

Conditions of Example 1 were replicated, except for the variations indicated herein.

Ampoule contents of the biological indicator of the invention were as follows: Bromothymol blue was used as colorimetric component of the culture medium and 0.1 mg/ml 8-anilinonaphthalene-1-sulfonic acid as fluorophore. 0.5 g/ml albumin was employed as exogenous sensor protein.

Along with the ampoule, the carrier containing $2.5 \times 10^6$ CFU of *Geobacillus stearothermophilus* ATCC 7953 spores was laid inside the tube. Exposure times were conducted at 132° C.

| Exposure Time (seconds) | Positives Instant readout | Positives 7 days readout | Positives 20 min readout BIONOVA BT224 | Positives 7 days readout BIONOVA BT224 |
|---|---|---|---|---|
| 120 | 20/20 | 20/20 | 20/20 | 20/20 |
| 150 | 20/20 | 13/20 | 20/20 | 14/20 |
| 180 | 14/20 | 7/20 | 15/20 | 5/20 |
| 210 | 5/20 | 0/20 | 5/20 | 0/20 |
| 240 | 0/20 | 0/20 | 0/20 | 0/20 |

Example 3

Conditions of Example 1 were replicated, except for the variations indicated herein.

Ampoule contents of the biological indicator of the invention were as follows: 5-Bromo-4-chloro-3-indolyl β-D-galactopyranoside was used as colorimetric component of the culture medium and 0.1 mg/ml 8-anilinonaphthalene-1-sulfonic acid as fluorophore. 0.5 g/ml casein was employed as exogenous sensor protein.

Along with the ampoule, the carrier containing $2.5 \times 10^6$ CFU of *Geobacillus stearothermophilus* ATCC 7953 spores was laid inside the tube. Exposure times were conducted at 132° C.

| Exposure Time (seconds) | Positives Instant readout | Positives 7 days readout | Positives 20 min readout BIONOVA BT224 | Positives 7 days readout BIONOVA BT224 |
|---|---|---|---|---|
| 120 | 20/20 | 20/20 | 20/20 | 20/20 |
| 150 | 20/20 | 19/20 | 20/20 | 14/20 |

-continued

| Exposure Time (seconds) | Positives Instant readout | Positives 7 days readout | Positives 20 min readout BIONOVA BT224 | Positives 7 days readout BIONOVA BT224 |
|---|---|---|---|---|
| 180 | 16/20 | 5/20 | 15/20 | 5/20 |
| 210 | 6/20 | 0/20 | 5/20 | 0/20 |
| 240 | 0/20 | 0/20 | 0/20 | 0/20 |

Example 4

Conditions of Example 1 were replicated, except for the variations indicated herein.

Ampoule contents of the biological indicator of the invention were as follows: Bromothymol blue was used as colorimetric component of the culture medium and 0.1 mg/ml 8-anilinonaphthalene-1-sulfonic acid as fluorophore.

Along with the ampoule, the carrier containing $2.5 \times 10^6$ CFU of *Geobacillus stearothermophilus* ATCC 7953 spores and 0.5 g/ml casein as exogenous sensor protein was laid inside the tube. Exposure times were conducted at 132° C.

| Exposure Time (seconds) | Positives Instant readout | Positives 7 days readout | Positives 20 min readout BIONOVA BT224 | Positives 7 days readout BIONOVA BT224 |
|---|---|---|---|---|
| 120 | 20/20 | 20/20 | 20/20 | 20/20 |
| 150 | 20/20 | 17/20 | 20/20 | 14/20 |
| 180 | 15/20 | 4/20 | 15/20 | 5/20 |
| 210 | 6/20 | 0/20 | 5/20 | 0/20 |
| 240 | 0/20 | 0/20 | 0/20 | 0/20 |

Example 5

Conditions of Example 1 were replicated, except for the variations indicated herein.

Ampoule contents of the biological indicator of the invention were as follows: Bromothymol blue was used as colorimetric component of the culture medium and 0.1 mg/ml L-tyrosine-7-amido-4-methylcoumarin as fluorophore. 0.5 g/ml casein was employed as exogenous sensor protein.

Along with the ampoule, the carrier containing $2.5 \times 10^6$ CFU of *Bacillus subtilis* ATCC 35021 spores was laid inside the tube. Exposure times were conducted at 121° C.

In this example no BIONOVA BT224 biological indicators were used for testing during the example along with the present invention to obtain comparison data, given that BIONOVA BT224 indicators are only suitable for high exposition temperatures.

| Exposure Time (minutes) | Positives Instant readout | Positives 7 days readout |
|---|---|---|
| 2 | 20/20 | 20/20 |
| 3 | 20/20 | 16/20 |
| 4 | 10/20 | 3/20 |
| 5 | 4/20 | 0/20 |
| 6 | 0/20 | 0/20 |

The invention claimed is:

1. An indicator for determining the efficacy of a steam or heat sterilization process, comprising:
   a protein,
   a fluorophore,
   a colorimetric component,
   microbial spores, and
   a culture medium,
   wherein the fluorophore interacts with a first region of the protein before the sterilization process providing a first fluorescence emission intensity and interacts with a second region of the protein after the sterilization process providing a second fluorescence emission intensity, and wherein exposing said protein to heat disrupts the interaction of the first region of the protein and the fluorophore to permit the interaction of the second region of the protein and fluorophore, yielding a different and immediate optically detectable signal;
   and wherein the different and immediate optically detectable signal indicates the sterilization process was successful.

2. The indicator of claim 1, wherein the protein and the fluorophore are housed within a container.

3. The indicator of claim 1, wherein the protein is capable of differentially interacting with the fluorophore depending on the tridimensional structure of the protein.

4. The indicator of claim 3, wherein the tridimensional structure of the protein is related to the intensity of the immediate optically detectable signal.

5. The indicator of claim 1, wherein the protein is denatured by the heat sterilization process.

6. The indicator of claim 1, wherein the protein/fluorophore ratio is between 2:1 and 8:1.

7. The indicator of claim 1, wherein the immediate optically detectable signal is observed within 20 seconds after initiating a sterilization process.

8. The indicator of claim 1, wherein the protein comprises at least one of fibrin, elastin, casein, collagen, actin, keratin, albumin, lysozyme, amylase, pepsin, glucosidase, phosphatase, galactosidase, chymotrypsin and lipase.

9. The indicator of claim 1, wherein the protein comprises at least one of fibrin, elastin, casein, collagen, actin, keratin, and albumin.

10. The indicator of claim 1, wherein the protein comprises at least one of a lysozyme, amylase, pepsin, glucosidase, phosphatase, galactosidase, chymotrypsin and lipase.

11. The indicator of claim 1, wherein the fluorophore is selected from the group consisting of Nile red; coumarin 6H; coumarin 6; coumarin 30; coumarin 102; coumarin 153, 7-Amino-4-(trifluoromethyl) coumarin; 8-anilinonaphthalene-1-sulfonic acid; 7-hydroxy-4-(trifluoromethyl) coumarin; 4,4'-dianilino-1,1'-binaphthyl-5,5-disulfonic acid dipotassium salt; L-alanine-7-amido-4-methylcoumarin; L-proline-7-amido-4-methylcoumarin; L-tyrosine-7-amido-4-methylcoumarin; L-leucine-7-amido-4-methylcoumarin; and L-phenylalanine-7-amido-4-methylcoumarin.

12. The indicator of claim 1, wherein after the sterilization process the culture medium contacts the microbial spores and produces an optically detectable color shift in the presence of microbial growth.

13. The indicator of claim 1, wherein the colorimetric component comprises bromocresol purple, bromocresol green, phenol red, thymol blue, bromophenol blue, bromothymol blue, 6-chloro-3-indoxyl-alpha-D-glucopyranoside, 5-bromo-4-chloro-3-indolyl alpha-D-glucopyranoside, 6-chloro-3-indoxyl-beta-D-galactopyranoside, 5-bromo-4-chloro-3-indolyl beta-D-galactopyranoside, or 5-bromo-4-chloro-3-indoxyl phosphate.

14. The indicator of claim 1, wherein the colorimetric component is present in the culture medium.

15. The indicator of claim 1, wherein the protein is casein and the fluorophore is L-tyrosine-7-amido-4-methylcoumarin.

16. The indicator of claim 1, wherein the protein is albumin and the fluorophore is 8-anilinonaphthalene-1-sulfonic acid.

17. The indicator of claim 1, wherein the protein is casein and the fluorophore is 8-anilinonaphthalene-1-sulfonic acid.

18. A method of sterilizing an object, the method comprising:

placing the indicator of claim 1 and an object within a sterilizer, initiating a sterilization process, determining that the sterilization process was effective by reviewing the fluorescent intensity of the indicator, thereby sterilizing the object.

\* \* \* \* \*